US005382428A

United States Patent [19]

Livingston-Wheeler et al.

[11] Patent Number: 5,382,428

[45] Date of Patent: Jan. 17, 1995

[54] METHOD FOR PREPARING A PURIFIED EXTRACTION RESIDUE FRACTION AND ITS USE IN STIMULATING THE IMMUNE RESPONSE

[75] Inventors: Virginia Livingston-Wheeler, San Diego County, Calif.; John J. Majnarich, King County, Wash.

[73] Assignees: John J. Mainarich; Virginia Livingston-Wheeler, both of Redmond, Wash.

[21] Appl. No.: 336,567

[22] Filed: Apr. 11, 1989

Related U.S. Application Data

[63] Continuation of Ser. No. 150,512, Feb. 8, 1988, abandoned, which is a continuation of Ser. No. 935,123, Nov. 26, 1986, abandoned, which is a continuation of Ser. No. 712,468, Mar. 15, 1985, abandoned, which is a continuation of Ser. No. 523,679, Aug. 16, 1983, abandoned, which is a continuation-in-part of Ser. No. 255,678, Apr. 20, 1981, Pat. No. 4,410,510, which is a continuation-in-part of Ser. No. 128,919, Mar. 10, 1980, abandoned, which is a continuation of Ser. No. 957,206, Nov. 3, 1978, abandoned.

[51] Int. Cl.[6] .................... A61K 37/00; A61K 39/02; C12N 1/20; A01N 37/18

[52] U.S. Cl. .............................. 424/234.1; 424/282.1; 435/68.1; 435/71.1; 435/252.1; 514/2

[58] Field of Search ................. 424/92, 93 D; 435/68, 435/252.1, 253, 71.7; 514/2

[56] References Cited

U.S. PATENT DOCUMENTS 3,958,025 5/1976 Livingston .......................... 424/317

OTHER PUBLICATIONS

Livingston, et al., Trans. N.Y. Acad. Sci., vol. 36, p. 569 (1974).

Chen et al., Proc. Soc. Exp. Biol. and Med., vol. 152, pp. 408–410 (1976).

Maruo et al., Proc. Natl. Acad. Sci., vol. 76, pp. 6622–6626, 1979.

Acevedo et al., Cancer, vol. 41, pp. 1217–1229, 1978.

Acevedo et al., Injection and Immunity, vol. 24, pp. 920–924, 1979.

*Primary Examiner*—Douglas W. Robinson
*Assistant Examiner*—Deborah K. Ware
*Attorney, Agent, or Firm*—Seed and Berry

[57] ABSTRACT

A method is disclosed for preparing a purified extraction residue fraction (antigen) of a microorganism isolated from the blood or urine of a warm-blooded animal or tumor carried by a warm-blooded animal, the microorganism having the capacity to synthesize the polypeptide hormone known as "chorionic gonadotropin" in its total form or in its alpha and beta subunits. The purified extraction residue fraction is an activator and modulator of immunological response and is capable of evoking pronounced prophylactic and therapeutic effects against a variety of tumors in laboratory animals and man. The immune response is stimulated by administering an effective immuno-stimulating amount of the residue fraction and/or co-administering the residue fraction together with an adjuvant such as the complete Freund's adjuvant.

8 Claims, No Drawings

METHOD FOR PREPARING A PURIFIED EXTRACTION RESIDUE FRACTION AND ITS USE IN STIMULATING THE IMMUNE RESPONSE

CROSS-REFERENCE TO RELATED APPLICATION

This application is a continuation of U.S. application Ser. No. 07/150,512, filed Feb. 8, 1988, now abandoned, which is a continuation of U.S. patent application Ser. No. 935,123, filed Nov. 26, 1986, now abandoned under C.F.R. δ 1.62, which is a continuation of U.S. patent application Ser. No. 712,468, filed Mar. 15, 1985, now abandoned, which was a continuation of U.S. patent application Ser. No. 523,679, filed Aug. 16, 1983, now abandoned, which was a continuation-in-part (CIP) of U.S. patent application Ser. No. 255,678, filed Apr. 20, 1981, now U.S. Pat. No. 4,410,510, which was a continuation-in-part of U.S. Ser. No. 128,919, filed Mar. 10, 1980, now abandoned, which was a continuation of U.S. patent application Ser. No. 957,206, filed Nov. 3, 1978 now abandoned.

TECHNICAL FIELD

This invention relates to a method of preparing a water-soluble, purified extraction residue fraction (antigen) of a microorganism, the purified residue fraction itself, and its use alone or in combination with an adjuvant for stimulating the immunological response in warm-blooded animals against a variety of tumors.

BACKGROUND ART

The purified extraction residue fraction (antigen) of microorganisms described in detail hereafter has been found to be useful in the treatment of avian leukosis as well as in the treatment of warm-blooded animals, including man, by stimulation of their immune response against a variety of tumors. The microorganism from which the purified extraction residue fraction is obtained is a pleomorphic, refractile and filterable form of bacteria which has been repeatedly isolated from both human and animal malignant tissue and blood of tumor-bearing hosts. These bacteria have been described by many investigators, but not many agree on their taxonomy because of their pleomorphism. Using standard culture and fermentation techniques, they resemble common saphophytes. Their various growth phases have been described as viruses, depetheroids, micrococci, bacilli, and fungi. See V. W-C. Livingston and E. Alexander-Jackson, "A Specific Type of Organism Cultivated from Malignancy: Bacteriology and Proposed Classification," *Ann. N. Y. Acad. Sci.,* 174:636–654 (1970); G. J. Dominque and J. U. Schlegel, "Novel Bacterial Structures in Human Blood: Cultural Isolation," *Infection & Immunity,* 15:621–627 (1977); and V. W-C. Livingston and A. M. Livingston, "Some Cultural, Immunological and Biochemical Properties of *Progenitor Cryptocides,*" *Trans. N. Y. Acad. Sci.,* 36:569–582 (1974).

In 1970, Virginia Livingston-Wheeler and Eleanor Alexander-Jackson proposed a new taxon for this organism within the order Actinomycetale. They named the organism "*Progenitor cryptocides.*" *Progenitor cryptocides* has been repeatedly isolated from human and animal malignant tumors and has many interesting features, such as pleomorphism, intermittent acid-fastness, a unique ability to pass through bacterial filters, and the ability to produce chorionic gonadotropin. See V. W-C. Livingston and E. Alexander-Jackson, "A Specific Type of Organism Cultivated from Malignancy: Bacteriology and Proposed Classification," *Ann. N. Y. Acad. Sci.,* 174: 636–654 (1970); and V. W-C. Livingston and A. M. Livingston, "Some Cultural, Immunological and Bio-Chemical Properties of Progenitor Cryptocides," *Trans. N. Y. Acad. Sci.,* 36:569–582 (1974).

The avian leukosis complex comprises the neoplastic diseases of the hematopoietic system of the domestic chicken, together with several other neoplastic and non-neoplastic conditions which are related either etiologically or pathologically. The following diseases are included in the complex leukosis: lymphoid leukosis, erythroid leukosis, and myeloid leukosis. Diseases etiologically related to leukosis include sarcoma, neophroblastoma, endothelioma and osteopletrosis. Marek's disease includes the neural form, visceral form and ocular form. See *The Merck Veterinary Manual,* 3rd edition, Merck & Co. , Inc., New Jersey, pp. 1081–1091 (1976). Marek's disease, for example, is seen in birds three weeks of age onward to adults. The commonest is two to four months. Young chicks are more susceptible than older birds. Genetic factors strongly influence the response of birds to agents of the leukosis complex. See A. E. Churchill and P. M. Briggs, "Agent of Marek's Disease in Culture," *Nature,* London 215: 28–530 (1967), and J. J. Solomon, R. L. Witter, K. Nazerian and B. B. Burmester, "Studies on the Etiology of Marek's Disease: Ch. I. Propagation of the Agent in Cell Culture," *Proc. Soc. Exp. Biol. Med.,* 127:173–177 (1968). Avian leukosis is presumably caused by a group B herpes virus. See J. J. Solomon, R. L. Witter, K. Nazerian and B. B. Burmester, "Studies on the Etiology of Marek's Disease: Ch. II. Finding of Herpes Virus in Cell Culture," *Proc. Soc. Exp. Biol. Med.,* 127:177–182 (1968). A live but attenuated form of turkey herpes virus vaccine has been effective until recently in preventing the incidence of Marek's disease tumors; however, its effectiveness has markedly declined. The mechanism of protection is not clear. Birds vaccinated develop a viremia with the vaccine. See Kermani-ARAB, V. T. Moll, B. R. Cho, W. D. Davis and Y-S. Lu, "Effect of Cyclophosphamide on the Response of Chickens to a Virulent Strain of Marek's Disease Virus," *Infection & Immunity,* 12:1058–1064 (1975). A group of investigators have just recently reported protection of chickens against Rous sarcoma virus with the use of methanol extracts of BCG challenged with Rous sarcoma. They also reported that chickens with palpable tumors, and then treated, developed necrosis of the tumor. See Y. Markson, F. Doljansky and D. W. Weiss, "Effects of Prophylactic Treatment with the Methanol Extraction Residue Fraction of Tubercle Bacilli (MER) on the Development of Rous Sarcomas of Chickens Following Challenge with the Rous Sarcoma Virus," *Immunological Parameters of Host-Tumor Relationships,* Vol. 5, D. W. Weiss (Ed.), Academic Press, New York, pp. 51–59 (1978).

Treatment of warm-blooded animals by subcutaneous injection of the purified extraction residue fraction is based on stimulation of the immune response of the host to the injected substance. Immunotherapy is a therapeutic approach to the treatment of cancer which is based on the concept that there are distinctive antigens in or on most tumor cells that distinguish them from normal host cells. Most tumor immunologists favor the view that potentially malignant cells constantly arise in the body; but because of their foreign nature, they are normally eliminated by the body's immune system. On occasion, however, tumor cells escape this immune surveillance and continue to reproduce, resulting in cancer. The reasons for the failure of this normally efficient immune mechanism are not completely understood. The body's immune system is depressed in certain genetic immunodeficiency diseases, in various bacterial, fungal or viral infections, and in patients undergoing immunosuppressive radiation therapy.

Experimental studies in animals have demonstrated the antitumor potential of a number of immuno-stimulants, including live organisms of bacillus Calmette-Guerin (BCG), heat-killed cells of *Cornynebacterium parvum,* polynucleotides and the anthelmintic drug, levamisole.

Stimulation of host resistance may De detected in animal models that can, in fact, detect both immunostimulators and anti-cancer agents. This is accomplished by infecting warm-blooded animals, such as mice, either with a virus which produces the disease and a disease-related immunodepression or with a transplantable mammary tumor. Effective agents for their therapeutic value are recognized by their ability to restore or enhance the antibody response in the experimental animal. Another means of recognizing stimulation of the immune response is to measure increased antibody responses or increased protective effects produced by the co-administration of vaccines and "immunoadjuvants." Further discussions of the function of immune response, methods of stimulation, and testing may be found in the following references: "Stimulation of Humoral and Cellular Antibody Formation in Mice by Poly I:C," W. Turner, et al., *Proc. Soc. Exp. Biol. & Med.,* 133, 334–338 (1970), and "Humoral and Cellular Immune Responses in Susceptible and Resistant Strains of Mice Infected with Friend Leukemia Virus," W. S. Cezlowski, et al., *Proc. Soc. Exp. Biol. & Med.,* 146, 619–624 (1974).

The methanol extraction residue fraction of tubercle bacilli has been shown to be an activator and modulator of immunological responsiveness and capable of evoking pronounced therapeutic effects against a variety of tumors in laboratory mammals and man. See D. W. Weiss, "Non-specific Stimulation and Modulation of the Immune Response and of States of Resistance by the MER Fraction of Tubercle Bacilli," *Nat'l Cancer Inst Monogr.,* 35:157 (1972); D. W. Weiss, et al., "Nonspecific Stimulation of Antimicrobial and Antitumor Resistance and of Immunological Responsiveness by the MER Fraction of Tubercle Bacilli," in: A. Zuckerman and D. W. Weiss (Eds.), *Dynamic Aspects of Host-Parasite Relationships,* Vol. 1, Academic Press, New York, p. 163 (1973).

DISCLOSURE OF THE INVENTION

This invention is concerned with a method of stimulating the immune response in warm-blooded animals by administering to the animals an effective immunostimulating amount of a purified extraction residue fraction from a microorganism isolated from the blood or urine of a warm-blooded host or a malignant tumor of a host and/or co-administering such purified extraction residue with an adjuvant. The microorganism should have the capacity to synthesize the polypeptide hormone known as "chorionic gonadotropin" in its total form or in its alpha and beta subunits. In particular, this invention is concerned with a method of stimulating the immune response in the avian species, such as domestic chickens, to avian leukosis by co-administering to the chickens an effective immunostimulating amount of a purified extraction residue fraction of the microorganism *Progenitor cryptocides* and an adjuvant. The invention is also concerned with a method of preparing the purified extraction residue fraction from the microorganism and the residue fraction per se.

It is thus a principal object of this invention to provide a method for stimulating the immune response in warm-blooded animals by administering to the animal an effective immunostimulating amount of a water-soluble, purified extraction residue fraction of the microorganism *Progenitor cryptocides* and/or co-administering such purified extraction residue with an adjuvant.

It is a further object of this invention to provide a method of treating domestic chickens to prevent their developing arian leukosis or diseases etiologically related to avian leukosis.

It is a further object of this invention to provide a method of preventing Marek's disease in domestic chickens by inoculating the chickens with a purified extraction residue fraction of the microorganism *Progenitor cryptocides* with an adjuvant.

It is a further object of this invention to produce a purified extract residue fraction of *Progenitor cryptocides,* the fraction containing the distinctive antigen of the *Progenitor cryptocides* which induces the formation of antibodies when injected into a warm-blooded host. "Antibodies," as used here, is intended to mean the specialized proteins genetically programmed to closely fit the antigen that stimulated their production.

BEST MODE FOR CARRYING OUT THE INVENTION

Evidence for the etiological relationship of *Progenitor cryptocides* to neoplastic disease has been documented over a period of years, as previously referenced. Its cultural properties, staining characteristics, and morphology have been fully described. Its filterable bodies have been measured by electron microscope and found similar in size to some viruses. The pathology produced in experimental animals has been reported. It has also been demonstrated in fresh blood samples examined by dark-field and phase microscopy. Also, the production by *Progenitor cryptocides* in vitro of a parahormone or analog or human chorionic gonadotropin has been described and confirmed by several investigators. See H. Cohen and A. Strampp, "Bacterial Synthesis of Substance Similar to Human Chorionic Gonadotropin," *Proc. Soc. Exp. Biol. Med.,* 152:408–410 (1976); H. F. Acevado, M. Slifkin, G. R. Pouchet and M. Pardo, "Immunohistochemical Localization of a Choriogonadotropin-like Protein in Bacteria Isolated from Cancer Patients," *Cancer,* 41:1217–1229 (1978); L. F. Affronti, L. Grow, R. Brumbough and K. Orton, "Production of Human Gonadotropin-like Substance by Bacterial Tumor Isolates," *Alesh. Ann. Meeting Am. Soc. Micro.* 1977, p. 84, New Orleans; T. Maruo, H. Cohen and S. S. Kolde, "Studies on Choriogonadotropin from a Microorganism", *Abst.* 951, The Endocrine Society, 61st Annual Meeting, June 13–15, 1979; and P. H. Lange, T. R. Hakala and E. E. Fraley, "Suppression of Antitumor Lymphocyte Mediated Cytotoxicity by Human Chorionic Gonadotropins," *J. Urology,* 115:95–98 (1976). *Progenitor cryptocides* is found is practically all warm-blooded animals with cancer. Heavy chemotherapy and/or antibiotic therapy suppress the microorganism, but never destroy it. All isolates used in the studies detailed in this application came from either direct blood cultures or mid-stream urine specimens of human patients. *Progenitor cryptocides* used in the present invention has the following morphological, cultural and physiological characteristics:

| | |
|---|---|
| Early culture fast growing: | Short rods and cocci - gram variable<br>Cocci 0.5–0.6 micron diameter, predominantly in clusters, non-motile |
| Gram reaction: | Gram positive |
| Ziehl-Neelsen stain: | Variable acid-fast, depending upon amount of mycolic acid present |
| Coagulase: | Negative |
| Mannitol: | |
| Acid aerobically | Positive |
| Acid anerobically | Negative |
| Heat-resistant endonucleases: | Positive |
| Biotin requirement: | Positive |
| Cell wall: | |
| Ribitol | Positive |
| Glycerol | Positive |
| Mycolic acid | Positive |
| Acetoin from glucose: | Positive |
| Chorionic gonadotropin: | Positive (In trypticase soy broth cultures at five days) as determined by pregnancy test kit and RIA |
| Gelatin stab.: | White surface growth with slow saccate liquefaction |
| Agar colonies: | Circular, smooth, generally pale, translucent white |
| Broth containing a fermentable carbohydrate: | Heavy, uniform turbidity with a ring pellicle |
| Litmus milk: | Acid |
| Carbohydrate fermentation: | No gas production from any sugar |

| | Acid Production | Gas Production |
|---|---|---|
| glucose | + | − |
| fructose | + | − |
| maltose | + | − |
| sucrose | + | − |
| trehalose | + | − |
| glycerol | + | − |
| galactose | − | − |
| lactose | + | − |
| xylose | − | − |
| arbinose | − | − |
| raffinose | − | − |
| inulin | − | − |
| sorbitol | − | − |
| Temperature optimum: | 37° C. | |

Appearance of Progenitor Cryptocides on Blood Agar Plate (1) White discoidal, often hemalytic, with a raised center giving a fried-egg appearance.
(2) Grayish mucoid, often confluent.
(3) Pigmented: occasionally sulfur yellow, sometimes a pink-to-orange variant seen.
(4) Wrinkled intermediate "worm cast," rough dull granular with irregular edges, often hemalytic, resembling B. subtilus.
(5) The organism is virulent to mice.
(6) In AJ Broth*, produces a characteristic white rim or soft pellicle.
(7) Sometimes dwarf colonies appear.

*Alexander-Jackson's broth. Ingredients: distilled water—2000 ml; beef lung (cut up)—2 pounds; peptones—20 grams: 5 grams each of (a) myosate, (b) gelysate, (c) trypticase, and (d)phytone; glucose—10 grams; and glycerol—80 ml. The broth is prepared by boiling the beef lung in water for thirty minutes. It is then filtered through cotton or very coarse paper into a flask containing the other ingredients and the mixture is heated. The crude lung broth can be autoclaved and stored in the icebox and clarified subsequently. It is clarified by depositing a 1-2 mm layer of Infusorial Earth (standard filter cel of Johns-Manville & Company) on a No. 42 Whatman paper disk by laying the disk on a Buchner funnel, applying suction, and then carefully pouring about 500 ml of a 5% suspension of filter cel. After deposition of the layer (when the water goes through clear), the suction flask is rinsed out. The hot medium, as prepared, is then filtered through the prepared disk into the flask. The pH of the medium is adjusted to 7.4 with sodium hydroxide and then tubed into screw-top glass tubes which are autoclaved. AJ broth is obtainable from the Colorado Serum Company, Denver, Colo.

Based upon taxonomic studies, *Progenitor cryptocides* has been identified as an actinomycete. A culture thereof has been placed on deposit with the American Type Culture Collection, and has been assigned No. 31874. Access to the culture is available during pendency of the application under 37 C.F.R. 1.14 and 35 U.S.C. § 122. All restrictions on the availability to the public of the culture deposited will be removed upon granting of the patent.

*Progenitor cryptocides* is frequently confused with *Staphlococcus epidermidis.* There is one unique difference in the two organisms. *Progenitor cryptocides* produces chorionic gonadotropin in vitro, which is not true of *Staphlococcus epidermidis.* In addition, *Progenitor cryptocides* has another unique property in that it is intermittently acid-fast. *Progenitor cryptocides* produces acid from glucose, lactose and maltose in the presence or absence of air. Acid is produced from glycerol and manitol only under aerobic conditions. No acid is produced from arabinose, cellobiose, inulin, raffinsoe, rhamnose, salicin, sorbitol or zylose under aerobic or anerobic conditions. Starch and esculin are not hydrolyzed. Growth in broth produces a mucoid deposit. The organism is gram positive in the rod form, but can be variable.

The purified extract residue fraction of *Progenitor cryptocides* containing the antigen of the organism is prepared by culturing the organism in a culture media; killing the microorganism; boiling the cells of the microorganism to dissolve the soluble portion of the microorganism, including the cell wall, to release the water-soluble antigen; discarding the heat denatured protein layer, leaving a clear filtrate containing the antigen; precipitating the antigen contained in the filtrate; and separating and purifying the precipitate from the remaining solution. Methanol or, preferably, ethanol or acetone may be used for precipitating the antigen from the remaining solution. Ethanol is preferred.

The purified extract residue fraction is redissolved in a physiological saline solution for subcutaneous injection into the warm-blooded host in amounts effective to stimulate an immunological response in the host.

It is preferable to co-administer the purified extract residue fraction or antigen with an adjuvant, such as Freund's complete adjuvant on an adjuvant prepared from muramyl dipeptide or synthetic muramyl dipeptide analogs. The preparation of Freund's complete adjuvant and the dosage regimen are described in Appendix 3 of D. M. Weir, *Handbook of Experimental Immunology* (3rd Ed., 1979), hereby incorporated by reference. The use of active adjuvant muramyl dipeptide derivatives to stimulate the resistance of animals to microbial infections is discussed in *Infection and Immunity* (Dec. 1982), pp. 848–854, also incorporated by reference.

The following examples illustrate the present invention and should not be construed as limiting its scope.

EXAMPLE 1

A sample of *Progenitor cryptocides* obtained as an isolate from a cancer patient by methods referenced previously was tested for positive production of chorionic gonadotropin-like hormone. The organism was cultured in a liquid media consisting of 17 grams of trypticase soy obtained from the Baltimore Biological Laboratory, Cockeysville, Md.; 10 grams yeast extract (BBL) and 2.5 grams of $K_2HPO_4$ per liter. The pH of the liquid media was 7.2. The cultures of the organism were maintained on Mueller-Hinton slants. Overnight growth of the organism was the usual inoculum source. Slants of the organisms were kept in the refrigerator at 5° C. for future reference.

250 ml of the above liquid media were put in 500 ml Erlenmeyer flasks. Each flask was inoculated from a single colony from a Mueller-Hinton slant or Mueller-Hinton plate.

Fermentation Conditions. A 20-liter lot of the above trypticase-yeast extract medium was employed in a 28-liter fermenter (New Brunswick Scientific Company, Edison, N.J.). The temperature of the fermenter was maintained at 37° C., with agitation set at 400 rpm. Sparging of the solution of broth was maintained at a rate of 10 liters of air per minute. The media was sterilized at 15 pounds pressure, 250° F., for 45 minutes, and then cooled and inoculated with an overnight (12 hours) 250 ml shake flask containing the organism. After fermentation for 20 hours, new media was introduced at the rate of 6 liters per hour. The new sterile media was supplemented with 3.5% dextrose. The fermenter was equipped with pH control so that sterile 5N sodium hydroxide could be added on a demand basis to maintain the pH at 7.2.

The harvest pump was set to pump at 6 liters per hour; thus the addition of new media and the harvest rate were set at the log phase of the organism. The harvested culture was centrifuged at 18,000 rpm with a continuous-flow Cepa centrifuge Model Z41. After 120 hours at 28° C., with the air source being a vacuum pump equipped with a glass wool filter previously sterilized, a fresh culture of *Progenitor cryptocides* was obtained as a paste, 25% solids. The yield was 40 g/l.

The media and the organism were then treated with 0.3% formalin to kill the organism. The media and growth with the added formalin were allowed to stand for several hours at room temperature and then centrifuged in a Sharples centrifuge to collect the dead cells. 200 grams of cells, wet weight, were collected. The dry weight solids of this mass of cells was 24.8% of the wet weight. The cells were adjusted to pH 5.0 with hydrochloric acid and a suspension of the cells in water brought to boiling with constant stirring and allowed to boil for 30 minutes. Upon cooling to room temperature, the mixture was centrifuged and the denatured protein layer was discarded. The remaining clear filtrate, containing the extract residue fraction of *Progenitor cryptocides,* including the antigen, was treated with 8 l absolute ethanol to precipitate the antigen. A white, water-soluble precipitate was obtained which was centrifuged and washed again with absolute ethanol. The precipitate was collected and dissolved in saline solution, 0.9% sodium chloride containing 0.5% phenol. The final solution contained 1 mg/cc of the alcohol-insoluble material. Analysis of the alcohol-insoluble material indicated that it was a lipopolysaccharide material. The nitrogen content of the material was determined by the micro-Kjeldahl method. Carbohydrate content was estimated by the method of Dubois. This was used in the following animal studies.

Swiss-Webster mice weighing 18–20 grams were purchased from Simonsen Laboratories, Gilroy, Calif. All of the animals were males. Each group had six to ten animals per group. In most of the animal studies, a Sarcoma 180 obtained from Dr. Chester Stock of Sloan-Kettering Memorial Research Laboratories was used. The tumor was maintained as an ascites by passage weekly in the mice. The inoculum was prepared by aspirating a mouse with a seven-day ascites into a sterile syringe and diluting the cells with sterile saline to obtain a suspension of $1\text{–}2\times10^6$ cells per $mm^3$. This suspension of cells was used to inoculate the mouse in the left hind leg (hamstring muscle) with 0.1 ml with ascitic tumor suspension. All of the inoculated mice were then placed in a large cage and segregated at random into groups of eight to ten mice. Treatment was started on day one, the day after tumor transplantation, and continued For a total of five days. All of the mice were sacrificed on day fourteen or fifteen, and the weight of the excised tumor determined. The mice were killed by cervical dislocation and the left hind leg removed at the hip joint. The skin was removed to expose the tumor. In many experiments, the right hind leg was also removed in a similar manner and weighed. By subtracting the weight of the normal leg from the tumor leg, the absolute tumor weight was determined. The dose of the purified extract residue fraction is given in the following table. It can be seen that the purified extract residue fraction of *Progenitor cryptocides* is effective in inhibiting the growth of the mouse tumors. The treated and controlled animals received 0.1 ml doses of respective material intraperitoneally.

TABLE I

Tumor, Sarcoma 180, Swiss-Webster Mice

| Treatment | No. Experiments | No. Mice | % Inhibition Range |
|---|---|---|---|
| Control | 11 | 110 | 0 |
| 0.1 ml (PA) for five days | 11 | 115 | 42–79 |

Similar experiments were carried out in the manner described previously with different tumor tissue types. The results are given in Table II, Table III, Table IV and Table V.

TABLE II

Tumor, Sarcoma 180, Ascites, Swiss-Webster Mice

| Treatment | No. Experiments | No. Mice | % Inhibition Range |
|---|---|---|---|
| Control | 5 | 60 | 0 |
| 0.1 ml (PA) for five days | 5 | 60 | 68–72 |

TABLE III

Tumor, Sarcoma 91, Melanoma, CDF-1 Mice

| Treatment | No. Experiments | No. Mice | % Inhibition Range |
|---|---|---|---|
| Control | 7 | 80 | 0 |
| 0.1 ml (PA) for five days | 7 | 80 | 28–30 |

TABLE IV

| Tumor, T-241, G57 Mice | | | |
|---|---|---|---|
| Treatment | No. Experiments | No. Mice | % Inhibition Range |
| Control | 5 | 50 | 0 |
| 0.1 ml (PA) for five days | 5 | 49 | 34-58 |

TABLE V

| Tumor, 1498 Leukemia, C-57 Mice | | | |
|---|---|---|---|
| Treatment | No. Experiments | No. Mice | % Inhibition Range |
| Control | 5 | 78 | 0 |
| 0.1 ml (PA) for five days | 5 | 79 | 65-71 |

EXAMPLE 2

Sixty eight-week-old leghorn chickens which had been inoculated with 0.5 ml purified extract residue fraction of *Progenitor cryptocides*, prepared as previously described, were randomly divided into 20 control birds and 40 test birds and housed in cages containing two birds each. The control and test birds were in the same room but were not allowed direct or indirect contact with each other. The birds were allowed free choice of water and feed.

The test birds were inoculated subcutaneously with a cell-associated, highly oncogenic Marek's disease virus and the controls with sterile physiological saline. The seed virus was obtained from Dr. J. M. Sharma, Regional Poultry Research Laboratory, East Lansing, Mich. The virus was grown in chick embryo fibroblast (CEF) tissue culture, harvested, sealed in five ampules of 0.6 ml each, and frozen in liquid nitrogen. Prior to inoculation of the test birds, the virus was tested for virulence and a titer established in CEF tissue culture as $30\times10^4$ plaque-forming units per 0.1 ml. At the time of inoculation, each arepule was thawed in ice water and diluted 1:6 in tissue culture medium containing 10% fetal calf serum. Each test bird was then inoculated subcutaneously with 0.2 ml of diluted virus to provide a final inoculation dose of 10,000 PFU/bird (plaque-forming units).

Three weeks post inoculation, 10 of the control birds and 20 of the test birds were necropsied. The remaining 10 controls and 20 test birds were necropsied six weeks post inoculation.

None of the control or test birds died during the test. When necropsied, none of the three- or six-week post inoculated birds or their controls had any gross lesions characteristic of Marek's disease.

In the three-week post exposure group, all of the birds had some lesions suggestive of Marek's virus infection. Twenty-five percent of the test animals had one to three tissues with mild lesions suggestive of exposure to Marek's disease. Seventy-five percent of the birds had lesions in four to six tissues which were compatible with Marek's disease. The control birds had 30% which were free of any evidence of infection with Marek's virus and 70% with mild lesions suggestive of exposure to Marek's virus.

RESULTS

In the six-week post exposure group, all of the birds had some lesions suggestive of Marek's virus infection. The lesions were milder in the six-week post inoculum group, with 9% of the birds having only one to three tissues with mild lesions suggestive of exposure to Marek's virus. Only one bird (5%) had lesions in four tissues which were compatible with a diagnosis of Marek's disease.

DISCUSSION

None of the birds inoculated with a highly oncogenic Marek's disease virus died or developed grossly observable lesions. Microscopic lesions either suggestive of or compatible with infection by Marek's virus were present in all inoculated test birds. The lesions were more prominent in the birds necropsied at three weeks post inoculation, with 25% having mild lesions suggestive of exposure to Marek's virus and 75% having lesions compatible with Marek's disease. In the birds necropsied six weeks post inoculation, 95% had mild lesions suggestive of exposure to Marek's virus and 5% had lesions compatible with a diagnosis of Marek's disease.

The control birds necropsied three weeks following a sham injection had 30% with no lesions and 70% with mild lesions. The controls necropsied at six weeks had 10% with no lesions and 90% with mild lesions.

This test indicates that the birds are protected against exposure to Marek's virus.

EXAMPLE 3

Of 60 five-week-old white leghorn chickens, 30 were vaccinated with two doses (each 0.1 ml) of the purified extract residue fraction of *Progenitor cryptocides* at two-week intervals. Thirty chickens were unvaccinated. All of the birds were raised in wire cages with two birds per cage. The control and test birds were housed in the same room. The birds were allowed water and feed (Purina Crumbles) ad libitum.

The test and control birds were inoculated subcutaneously with a cell-associated, highly oncogenic Marek's disease virus. The virus was grown in chick embryo fibro-blast (CEF) tissue culture, harvested, sealed in five ampules of 0.6 ml each, and frozen in liquid nitrogen. Prior to inoculation of the test birds, the virus was tested for virulence and a titer established in CEF tissue culture as $30\times10^4$ plaque-forming units per 0.1 ml. At the time of inoculation, each ampule was thawed in ice water and diluted 1:6 in tissue culture medium containing 10% fetal calf serum. Each test bird was then inoculated subcutaneously with 0.2 ml of diluted virus to provide a final inoculation dose of 10,000 PFU/bird (plaque-forming units). The birds were observed daily and the mortalities were recorded.

RESULTS

The birds were observed for a period of six weeks. Post inoculation and mortalities were recorded.

| | MORTALITIES | |
|---|---|---|
| No. Birds/Group | Vaccinated Group | Non-vaccinated Group |
| 30 | 1 | 26 |

The surviving birds were sacrificed and examined for gross lesions of Marek's disease. All of the chickens appeared to be free of the disease.

| No. Birds/Group | MORTALITIES Vaccinated Group | Non-vaccinated Group |
|---|---|---|
| 30 | 2 | 28 |

The experiment was repeated. The results after six weeks were as follows:

| No. Birds/Group | MORTALITIES 1 Injection | 2 Injections | 0 Injection |
|---|---|---|---|
| 25 | 8 | 4 | 25 |

EXAMPLE 4

The antibody response of warm-blooded animals injected intraperitoneally with the purified extract residue of *Progenitor cryptocides* was subjected to a nemaglutinin test to determine the effect of the treatment on the antibody response. The tests were performed by standard procedures using the microtiter plate technique. Acceptable hemaglutinin titer for the average mouse ranges from 1:64 to 1:128. A stock culture of *Progenitor cryptocides* was grown overnight in broth as previously described. Depending upon the number of samples to be run, several tubes were utilized. The broth cultures were centrifuged and the broth decanted off. The cells were washed twice in PBS and resuspended in PBS to absorbency of approximately 0.75 (0.65 minimum, 0.8 maximum) at 520 mm. 0.05 ml PBS was added to all wells in a "U"-bottom microtiter plate using a standardized pipette. 0.05 ml of serum obtained from the blood of the warm-blooded animals injected with the purified extract residue of *Progenitor cryptocides* were added to every other well at the head of the column. The serum was diluted with 0.05 ml microdiluter down column. 0.05 ml of cell suspension was added to all wells. All the samples were incubated at room temperature for 30–60 minutes and refrigerated overnight.

EXAMPLE 5

Approximately 200-day old white leghorn chickens were housed ten to a cage. The control and test birds were in the same room but were not allowed direct or indirect contact with each other. The birds were allowed free choice of water and feed. The birds were fed a commercial chicken broiler ration. Of the approximate 200 birds, only 30 were vaccinated with the conventional wild turkey virus in the conventional manner. The remaining birds were treated only once a day 7 with 0.2 ml of the control saline solution, the purified extract residue fraction of *Progenitor cryptocides* as previously described, a 50:50 mixture of the purified antigen plus complete Freund's adjuvant as purchased from Cal-Biochem mixed with the purified antigen just before use, and the complete Freund's adjuvant alone.

The test birds were challenged with Marek's disease preparation, as previously described in Example 2, at four weeks of age. The Marek's disease preparation contained 1500 CFU (colony forming units). A summary of the treatment and mortalities over a 12-week period is given in the following table.

| TREATMENT | No. BIRDS | SUMMARY OF TREATMENT AND MORTALITIES MORTALITY 4–12 Weeks | POST MORTEM Sacrifice 12 Weeks No. Evidence Marek's | TOTAL MORTALITIES Plus birds with Marek's at Sacrifice | Per Cent WITH MAREK'S |
|---|---|---|---|---|---|
| Control Saline, Phenol 0.2 ml | 30 | 21 | 5 | 26 | 86 |
| Purified antigen only | 24 | 4 | 3 | 7 | 29 |
| Purified antigen + Freund's adjuvant | 29 | 0 | 0 | 0 | 0 |
| Freund's adjuvant | 22 | 6 | 3 | 9 | 40 |
| Wild turkey virus only | 30 | 4 | 3 | 7 | 23 |

We claim:

1. A method of preparing an antigenic fraction of a *Progenitor cryptocides* microorganism having all of the essential characteristics of ATCC Deposit Accession No. 31874, isolated from a warm-blooded animal or malignant tumor of a warm-blooded animal, the microorganism having the capacity to synthesize the polypeptide known as "chorionic gonadotropin" in its total form or in its alpha and beta subunits, comprising:
   culturing the microorganism in an appropriate culture media,
   separating the microorganism from the culture media,
   extracting the antigenic fraction of the microorganism, and
   recovering the antigenic fraction.

2. The method of claim 1 wherein the antigenic fraction is extracted by heating a suspension of the microorganism, resulting in at least a partial dissolution of the microbial cell walls, and separating the cellular fraction from the antigenic fraction and recovering the antigenic fraction.

3. The method of claim 1 wherein the microorganism is killed prior to separating the microorganism from the culture media.

4. The method of claim 1 wherein the antigenic fraction is recovered by precipitation with absolute ethanol.

5. The method of claim 2 wherein the suspension has been adjusted to about pH 5 prior to heating.

6. A method of immunizing domestic chickens to confer resistance to avian leukosis virus, comprising:
   preparing an antigenic fraction of a *Progenitor cryptocides* microorganism having all of the essential characteristics of ATCC 5Deposit Accession No. 31874 by culturing the microorganism in an appropriate culture medium, separating the microorganism from the culture medium, extracting the antigenic fraction of the microorganism, and recovering the antigenic fraction; and
   administering an effective amount of the antigenic fraction to the chickens.

7. The method of claim 6 wherein the antigenic fraction is coadministered with an adjuvant.

8. The method of claim 7 wherein the adjuvant is Freund's adjuvant.

* * * * *